US007718365B2

(12) United States Patent
Wang

(10) Patent No.: US 7,718,365 B2
(45) Date of Patent: *May 18, 2010

(54) MICROARRAY ANALYSIS OF RNA

(75) Inventor: Hui Wang, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 52 days.

This patent is subject to a terminal disclaimer.

(21) Appl. No.: 11/178,064

(22) Filed: Jul. 9, 2005

(65) Prior Publication Data

US 2007/0009915 A1 Jan. 11, 2007

(51) Int. Cl.
*C12Q 1/68* (2006.01)
*C12P 19/34* (2006.01)
*C07H 21/02* (2006.01)

(52) U.S. Cl. .................. 435/6; 435/91.1; 435/91.32; 536/23.1; 536/24.3

(58) Field of Classification Search .............. 435/6, 435/91.1, 91.32; 536/23.1, 24.3
See application file for complete search history.

(56) References Cited

U.S. PATENT DOCUMENTS

| 5,525,468 A * | 6/1996 | McSwiggen ............ 435/6 |
|---|---|---|
| 5,573,913 A | 11/1996 | Rosemeyer et al. |
| 6,992,180 B1 | 1/2006 | Engelhardt et al. |
| 2001/0014446 A1 | 8/2001 | Heroux et al. |
| 2003/0190661 A1 | 10/2003 | Gruber et al. |
| 2004/0180362 A1* | 9/2004 | Lazar et al. ............ 435/6 |
| 2006/0160096 A1 | 7/2006 | Cole et al. |

FOREIGN PATENT DOCUMENTS

| WO | WO 94/12518 | | 11/1993 |
|---|---|---|---|
| WO | WO 01/32672 | * | 5/2001 |
| WO | WO 02/16647 | * | 2/2002 |
| WO | WO2005/054466 A2 | | 7/2004 |

OTHER PUBLICATIONS

Liu et al, An oligonucleotide microchip for genome wide microRNA profiling in human and mouse tissues, 2004, 101, 9740-9744, Published on line on Jun. 21, 2004.*
Affymetrix GeneChip *E.coli* antisense genome array expression analysis protocol, 2001.*
Affymetrix Genechip *E. coli* genome probe array, Apr. 4, 2000.*
Affymetrix P/N 510051 array brochure.*
Shine et al, The 3' terminal of *E. Coli* 16 S ribosomal RNA: Complementary to nonsense triplets and ribosome binding sites, 1974, PNAS, 71, 1342-1346.*
Ularich Lehmann and Hans Kreipe.Real-time PCR analysis of DNA and RNA Extracted from Formalin-fixed and Praffin-Embedded Biopsies, Real-Time PCR and Archival Biopsies, A Companion to Methods in Enzymology, Academic Press Inc., NY, NY, US vol. 25, No. 4, Dec 2001 pp. 409-412, XP00230656.
Richard Cosstick, et al., "Fluorescent labeling of tRNA and oligodeoxynucleotides using T4 RNA ligase", Nucleic Acids Research, vol. 12, No. 4, 1984, pp. 1791-1810.
Jorge R. Barrio, et al., "Synthesis of Modified Nucleoside 3', 5' —Bisphosphates and their Incorporation into Oligoribonucleotides with T4 RNA Ligase", Modified Oligoribonucleotides, vol. 17, No. 11, 1978 pp. 2077-2081.
Wang, H., et al., "Direct and sensitive miRna profiling from low-input total RNA", vol. 13, Nov. 14, 2006, pp. 1-9, XP002408565.
European Search Report EP 06 25 3554 dated Nov. 28 2006.
Kyle Cole, et al., "Direct labeling of RNA with multiple biotins allows sensitive expression profiling of acute leukemia class predictor genes", Nucleic Research, vol. 32, No. 11 Oxford University Press 2004; pp. 1-9.
Volker Lohman, et al., "Mutations in Hepatitis C virus RNAs Conferring Cell Culture Adaptation", Journal of Virology, Vo. 75, No. 3, Feb. 2001, pp. 1437-1449.
Ross W. Richardson, et al., "Biotin and fluorescent labeling of RNA using T4 RNA ligase", Nucleic Acids Research, vol. 11, No. 18, 1983, pp. 6167-6184.
Thomas E. England, et al., Enzymatic Olgoribonucleotide Synthesis with T4 RNA Ligase, American Chemical Society and reprinted by permission of the copyright owner, Reprinted from Biochemistry, 1978, pp. 2070-2076.
Thomas England, et al., "3'-Terminal Labeling of RNA with T4 RNA Ligase", Nature, vol. 275, Oct. 1978; Department of Biochemistry, University of Illinois, pp. 560-561.
Lance A. Bare, et al., "Specific Substitution into the Anticodon Loop of Yeast Tyrosine Transfer RNA", Biochemistry 1986, 25, pp. 5825-5830; 1986 American Chemical Society.
A. Gregory Bruce, et al., "Reactions at the terminal tRNA with T4 RNA ligase", Nucleic Acids Research, vol. 5, No. 10, Oct. 1978, pp. 3665-3677.
Paul J. Romanuk, et al., "Joining RNA Molecules with RNA Ligase", Methods in Enzymology, vol. 100 pp. 52-59. XP001248219.
Zhulidov, P., et al. Simple cDNA normalization using kamchatka crab duplex-specific nuclease. Nucleic Acids Research. 2004, vol. 32, No. 3, pp. e37.

* cited by examiner

*Primary Examiner*—Stephen Kapushoc
*Assistant Examiner*—Narayan K Bhat

(57) ABSTRACT

In certain embodiments, the invention provides a method of performing an array analysis, the method including contacting a sample of RNA with an analogous DNA set to provide a DNA/RNA duplex, contacting the DNA/RNA duplex with an enzyme having a DNA:RNA nuclease activity to provide a digested RNA sample, and contacting the digested RNA sample with an array under conditions sufficient to provide for specific binding to the array. The array typically is then interrogated. Kits in accordance with the invention are also described which include an analogous DNA set and an array.

24 Claims, 1 Drawing Sheet

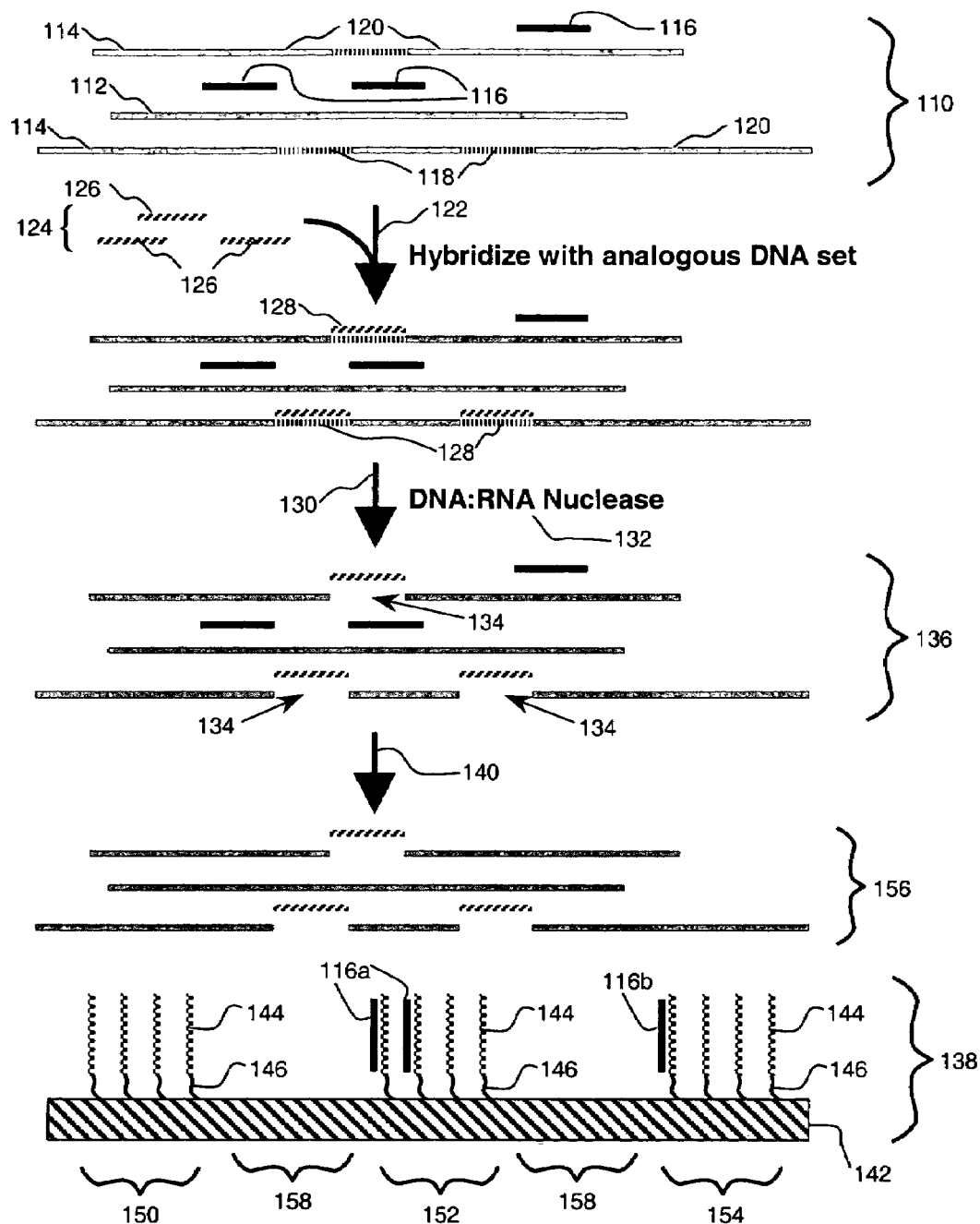
Figure

US 7,718,365 B2

MICROARRAY ANALYSIS OF RNA

RELATED APPLICATIONS

Related subject matter is disclosed in a U.S. patent application Ser. No. 11/177,679 by Wang entitled "Method of Treatment of RNA Sample", co-filed with the present application.

FIELD OF THE INVENTION

The invention relates generally to methods of biochemical analysis. More specifically, the invention relates to analysis of an RNA sample.

BACKGROUND OF THE INVENTION

There has been great interest in the analysis of small RNAs, such as short interfering RNAs (siRNAs), microRNAs (miRNA), tiny non-codingRNAs (tncRNA) and small modulatory RNA (smRNA), since the discovery of siRNA biological activity over a decade ago. See Novina et al., Nature 430: 161-164 (2004). Even though the functions of most discovered miRNAs remain a mystery, it has become clear that they exist in abundance in plants and animals, with up to tens of thousands of copies per cell. In the fruit fly, 78 have been identified, and over 200 have been identified in human (see the public database accessible via the website located at >>http://www.sanger.ac.uk/cgi-bin/Rfam/mirna/browse.pl<<). The levels of individual miRNAs seem to vary with developmental stages and tissue types. The level of fluctuation may be correlated with phenotype, mRNA levels, or protein levels for better biological insight. Thus quantitative measurements of miRNA may be of great importance. Further, viral miRNAs have been identified and may play a role in latency (see Pfeffer et al., Science, 304: 734-736 (2004)), making the detection and quantification of miRNAs a potentially valuable diagnostic tool.

Straightforward and reliable methods for simultaneously analyzing several constituents of a complex sample are extremely desirable. Analytical methods employing polynucleotide arrays have been used for investigating small RNAs, e.g. miRNAs have become a subject of investigation with microarray analysis. See, e.g., Liu et al., Proc. Nat'l Acad. Sci. USA, 101: 9740-9744 (2004); Thomson et al., Nature Methods, 1: 1-7 (2004); and Babak et al., RNA, 10: 1813-1819 (2004). Polynucleotide arrays (such as DNA or RNA arrays) are known and are used, for example, as diagnostic or screening tools. Such arrays include regions of usually different sequence polynucleotides ("capture agents") arranged in a predetermined configuration on a solid support. The arrays are "addressable" in that these regions (sometimes referenced as "array features") have different predetermined locations ("addresses") on the support of the array. The polynucleotide arrays typically are fabricated on planar supports either by depositing previously obtained polynucleotides onto the support in a site specific fashion or by site specific in situ synthesis of the polynucleotides upon the support. After depositing the polynucleotide capture agents onto the support, the support is typically processed (e.g., washed and blocked for example) and stored prior to use.

Generally, an array is contacted with a sample or labeled sample containing analytes (typically, but not necessarily, other polynucleotides) under conditions that promote specific binding of the analytes in the sample to one or more of the capture agents present on the array. Thus, the arrays, when exposed to a sample, will undergo a binding reaction with the sample and exhibit an observed binding pattern. This binding pattern can be detected upon interrogating the array. For example all target polynucleotides (for example, DNA) in the sample can be labeled with a suitable label (such as a fluorescent compound), and the label then can be accurately observed (such as by observing the fluorescence pattern) on the array after exposure of the array to the sample. Assuming that the different sequence polynucleotides were correctly deposited in accordance with the predetermined configuration, then the observed binding pattern will be indicative of the presence and/or concentration of one or more components of the sample. Techniques for scanning arrays are described, for example, in U.S. Pat. No. 5,763,870 and U.S. Pat. No. 5,945,679. Still other techniques useful for observing an array are described in U.S. Pat No. 5,721,435.

While current methods of analysis of RNA samples are quite useful, there is a continuing need for improved analytical methods, such as in array-based analysis of RNA.

SUMMARY OF THE INVENTION

Methods of performing an array analysis of an RNA sample are described. In certain embodiments, the invention provides a method of performing an array analysis wherein the method includes contacting the sample of RNA with an analogous DNA set to provide a DNA/RNA duplex. The analogous DNA set includes at least one sequence analogous to a small RNA. The DNA/RNA duplex is contacted with an enzyme having a DNA:RNA nuclease activity to provide a digested RNA sample. Then, the digested RNA sample is contacted with an array under conditions sufficient to provide for specific binding to the array. The array typically is then interrogated to provide information on binding of RNA in the sample to the array. In certain embodiments, the array is interrogated by measuring a signal from an observable label associated with the RNA bound to the array.

Kits in accordance with the invention are also described, wherein the kits include an analogous DNA set, wherein the analogous DNA set includes at least one sequence analogous to a small RNA; and an array having a plurality of capture agents, each of the plurality of capture agents specific for a small RNA.

Additional objects, advantages, and novel features of this invention are set forth in part in the description follows and in part will become apparent to those skilled in the art upon examination of the following specifications or may be learned by the practice of the invention. The objects and advantages of the invention may be realized and attained by means of the instruments, combinations, compositions and methods particularly pointed out herein and in the appended claims.

BRIEF DESCRIPTION OF THE DRAWINGS

These and other features of the invention will be understood from the description of representative embodiments of the method herein and the disclosure of illustrative apparatus for carrying out the method, taken together with the Figures, wherein The FIGURE schematically illustrates embodiments of the present invention.

The FIGURE components are broadly illustrative and are not drawn to scale.

DETAILED DESCRIPTION

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an oligodeoxynucleotide" includes a plurality of oligodeoxynucleotides. Similarly, reference to "an RNA" includes a plurality of different identity (sequence) RNA species.

Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation. In this specification and in the claims that follow, reference will be made to a number of terms that shall be defined to have the following meanings unless a contrary intention is apparent.

"Optional" or "optionally" means that the subsequently described circumstance may or may not occur, so that the description includes instances where the circumstance occurs and instances where it does not. For example, if a step of a process is optional, it means that the step may or may not be performed, and, thus, the description includes embodiments wherein the step is performed and embodiments wherein the step is not performed (i.e. it is omitted).

An "oligonucleotide" is a molecule containing from 2 to about 100 nucleotide subunits. An "oligodeoxynucleotide" is a molecule containing from 2 to about 100 deoxyribonucleotide subunits. The term "nucleic acid" and "polynucleotide" are used interchangeably herein to describe a polymer of any length composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner similar to that of two naturally occurring nucleic acids, e.g., can participate in Watson-Crick base pairing interactions. The terms "nucleoside", "nucleotide", "oligodeoxynucleotide", and "deoxyribonucleotides" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Modified nucleosides or nucleotides also include molecules having structural features that are recognized in the literature as being mimetics, derivatives, having similar properties, or other like terms, and include, for example, polynucleotides incorporating non-natural (not usually occurring in nature) nucleotides, unnatural nucleotide mimetics such as 2'-modified nucleosides, peptide nucleic acids, oligomeric nucleoside phosphonates, and any polynucleotide that has added substituent groups, such as protecting groups or linking moieties.

A duplex is a double stranded structure typically formed between complementary nucleic acid sequences. A DNA/RNA duplex is a double stranded structure formed between a DNA molecule and an RNA molecule. Similarly, an RNA/RNA duplex is a double stranded structure formed between an RNA molecule and another RNA molecule (or different portions of the same RNA molecule).

"Sequence" may refer to a particular sequence of bases and/or may also refer to a polynucleotide having the particular sequence of bases. Thus a sequence may be information or may refer to a molecular entity, as indicated by the context of the usage.

"Moiety" and "group" are used to refer to a portion of a molecule, typically having a particular functional or structural feature, e.g. a linking group (a portion of a molecule connecting two other portions of the molecule), or an ethyl moiety (a portion of a molecule with a structure closely related to ethane). A moiety is generally bound to one or more other moieties to provide a molecular entity. As a simple example, a hydroxyl moiety bound to an ethyl moiety provides an ethanol molecule. At various points herein, the text may refer to a moiety by the name of the most closely related structure (e.g. an oligonucleotide moiety may be referenced as an oligonucleotide, a mononucleotide moiety may be referenced as a mononucleotide). However, despite this seeming informality of terminology, the appropriate meaning will be clear to those of ordinary skill in the art given the context, e.g. if the referenced term has a portion of its structure replaced with another group, then the referenced term is usually understood to be the moiety. For example, a mononucleotide moiety is a single nucleotide which has a portion of its structure (e.g. a hydrogen atom, hydroxyl group, or other group) replaced by a different moiety (e.g. a linking group, an observable label moiety, or other group). Similarly, an oligonucleotide moiety is an oligonucleotide which has a portion of its structure (e.g. a hydrogen atom, hydroxyl group, or other group) replaced by a different moiety (e.g. a linking group, an observable label moiety, or other group). "Nucleotide moiety" is generic to both mononucleotide moiety and oligonucleotide moiety.

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

"Bound" may be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect. "Free," as used in the context of a moiety that is free, indicates that the moiety is available to react with or be contacted by other components of the solution in which the moiety is a part.

"Isolated" or "purified" generally refers to isolation of a substance (compound, polynucleotide, protein, polypeptide, polypeptide, chromosome, etc.) such that the substance comprises a substantial portion of the sample in which it resides (excluding solvents), i.e. greater than the substance is typically found in its natural or un-isolated state. Typically, a substantial portion of the sample comprises at least about 2%, at least about 5%, at least about 10%, at least about 20%, at least about 30%, at least about 50%, at least about 80%, or at least about 90% of the sample (excluding solvents). For example, a sample of isolated RNA will typically comprise at least about 2% total RNA, or at least about 5% total RNA, where percent is calculated in this context as mass (e.g. in micrograms) of total RNA in the sample divided by mass (e.g. in micrograms) of the sum of (total RNA+other constituents in the sample (excluding solvent) ). Techniques for purifying polynucleotides and polypeptides of interest are well known in the art and include, for example, gel electrophresis, ion-exchange chromatography, affinity chromatography, and sedimentation according to density. In typical embodiments, the sample or the enzyme having a DNA:RNA nuclease activity is in isolated form; more typically, both are obtained in isolated form prior to use in the present methods.

The term "sample" as used herein relates to a material or mixture of materials, typically, although not necessarily, in fluid form, containing one or more components of interest.

The term "analyte" is used herein to refer to a known or unknown component of a sample. In certain embodiments of the invention, an analyte may specifically bind to a capture agent on a support surface if the analyte and the capture agent are members of a specific binding pair. In general, analytes are typically RNA or other polynucleotides. Typically, an "analyte" is referenced as a species in a mobile phase (e.g., fluid), to be detected by a "capture agent" which, in some embodiments, is bound to a support, or in other embodiments, is in solution. However, either of the "analyte" or "capture agent" may be the one which is to be evaluated by the other (thus, either one could be an unknown mixture of components of a sample, e.g., polynucleotides, to be evaluated by binding with the other). "Target", or "target analyte" references an analyte that has a corresponding capture agent which specifically binds to that target analyte in a given binding assay, e.g. an array binding assay.

The term "capture agent" refers to an agent that binds an analyte through an interaction that is sufficient to permit the agent to bind and concentrate the analyte from a homogeneous mixture of different analytes. The binding interaction may be mediated by an affinity region of the capture agent. Representative capture agents include polypeptides and polynucleotides, for example antibodies, peptides, or fragments of double stranded or single-stranded DNA or RNA may employed. Capture agents usually "specifically bind" one or more analytes.

The terms "specific binding", "specifically bind", or like terms, refers to the ability of a capture agent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold). In certain embodiments, the binding constant of a capture agent and analyte is greater than $10^6$ $M^{-1}$, greater than $10^7 M^{-1}$, greater than $10^8 M^{-1}$, greater than $10^{15} M^{-1}$, greater than $10^{10} M^{-1}$, usually up to about $10^{12}$ $M^{-1}$, or even up to about $10^{15} M^{-1}$.

The term "stringent assay conditions" as used herein refers to conditions that are compatible to produce binding pairs of nucleic acids, e.g., capture agents and analytes, of sufficient complementarity to provide for the desired level of specificity in the assay while being incompatible to the formation of binding pairs between binding members of insufficient complementarity to provide for the desired specificity. Stringent assay conditions are the summation or combination (totality) of both hybridization and wash conditions.

A "stringent hybridization" and "stringent hybridization wash conditions" in the context of nucleic acid hybridization (e.g., as in array, Southern or Northern hybridizations, or hybridization of molecules in solution) are sequence dependent, and are different under different experimental conditions. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1× SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions may affect the degree to which nucleic acids are specifically hybridized to complementary capture agents. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 1 to about 20 minutes; or, multiple washes with a solution with a salt concentration of about 0.1×SSC containing 0.1% SDS at 20 to 50° C. for 1 to 15 minutes; or, equivalent conditions. Stringent conditions for washing can also be, e.g., 0.2×SSC/0.1% SDS at 42° C. In instances wherein the nucleic acid molecules are oligodeoxynucleotides (e.g. oligonucleotides made up of deoxyribonucleotide subunits), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

A specific example of stringent assay conditions is rotating hybridization at a temperature of about 55° C. to about 70° C. in a salt based hybridization buffer with a total monovalent cation concentration of 1.5M (e.g., as described in U.S. patent application Ser. No. 09/655,482 filed on Sep. 5, 2000, the disclosure of which is herein incorporated by reference) followed by washes of 0.5×SSC and 0.1×SSC at room temperature and 37° C.

Stringent hybridization conditions may also include a "pre-hybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA or with random sequence synthetic oligonucleotides (e.g. 25-mers), or the like.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

The term "pre-determined" refers to an element whose identity is known prior to its use. For example, a "pre-determined analyte" is an analyte whose identity is known prior to any binding to a capture agent. An element may be known by name, sequence, molecular weight, its function, or any other attribute or identifier. In some embodiments, the term "analyte of interest", i.e., a known analyte that is of interest, is used synonymously with the term "pre-determined analyte".

The term "array" encompasses the term "microarray" and refers to an ordered array of capture agents for binding to aqueous analytes and the like. An "array" includes any two-dimensional or substantially two-dimensional (as well as a three-dimensional) arrangement of spatially addressable regions (i.e., "features") containing capture agents, particularly polynucleotides, and the like. Any given support may carry one, two, four or more arrays disposed on a surface of a support. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than 100 cm$^2$, 20 cm$^2$ or even less than 10 cm$^2$, e.g., less than about 5 cm$^2$, including less than about 1 cm$^2$, less than about 1 mm$^2$, e.g., 100 µm$^2$, or even smaller. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of the same or different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Arrays can be fabricated by depositing (e.g., by contact- or jet-based methods) either precursor units (such as nucleotide or amino acid monomers) or pre-synthesized capture agent. An array is "addressable" when it has multiple regions of different moieties (e.g., different capture agent) such that a region (i.e., a "feature" or "spot" of the array) at a particular predetermined location (i.e., an "address") on the array will detect a particular sequence. An "array layout" refers to one or more characteristics of the features, such as feature positioning on the support, one or more feature dimensions, and an indication of a moiety at a given location. A "linker" is any moiety that binds to at least two other moieties, e.g. a capture agent may be bound to a support via a linker; such linker may be any such linker or "tether" known in the literature relating to arrays. "Interrogating" (or "reading") the array refers to obtaining information from the array, especially information about analytes binding to the array. "Hybridization assay" references a process of contacting an array with a mobile phase containing analyte. An "array support" refers to an article that supports an addressable collection of capture agents.

Interfering sequences: For convenience herein, sequences in a sample of RNA that are complementary to small RNAs are referenced as "interfering sequences".

Small RNA references RNAs less than about 500 bases long, e.g. less than about 400 bases long, less than about 300 bases long, less than about 200 bases long, less than about 100 bases long, less than about 60 bases long, less than about 50 bases long, less than about 40 bases long, or less than about 35 bases long. In particular embodiments, the small RNA may be selected from short interfering RNAs (siRNAs), microRNAs (miRNA), tiny non-coding RNAs (tncRNA) and small modulatory RNA (smRNA), or combinations thereof. See Novina et al., Nature 430: 161-164 (2004). In particular embodiments, small RNAs may be at least about 4 bases long, at least about 6 bases long, at least about 8 bases long, or longer.

"Complementary" references a property of specific binding between polynucleotides based on the sequences of the polynucleotides. As used herein, polynucleotides are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C. "Complementary" includes embodiments in which there is an absolute sequence complementarity, and also embodiments in which there is a substantial sequence complementarity. "Absolute sequence complementarity" means that there is 100% sequence complementarity between a first polynucleotide and a second polynucleotide, i.e. there are no insertions, deletions, or substitutions in either of the first and second polynucleotides with respect to the other polynucleotide (over the complementary region). Put another way, every base of the complementary region may be paired with its complementary base, i.e. following normal base-pairing rules. "Substantial sequence complementarity" permits one or more relatively small (less than 10 bases, e.g. less than 5 bases, typically less than 3 bases, more typically a single base) insertions, deletions, or substitutions in the first and/or second polynucleotide (over the complementary region) relative to the other polynucleotide. The complementary region is the region that is complementary between a first polynucleotide and a second polynucleotide (e.g. a target analyte and a capture agent; further e.g. an oligodeoxynucleotide that is analogous to a small RNA and an interfering sequence that is complementary to the small RNA). Complementary sequences are typically embedded within larger polynucleotides, thus two relatively long polynucleotides may be complementary over only a portion of their total length. The complementary region is typically at least about 10 bases long, more typically at least about 12 bases long, more typically at least about 15 bases long, still more typically at least about 20 bases long, or may be at least about 25 bases long. In various typical embodiments, the complementary region may be up to about 200 bases long, or up to about 120 bases long, up to about 100 bases long, up to about 80 bases long, up to about 60 bases long, up to about 45 bases long, or up to about 40 bases long.

Sequence complementarity between two nucleic acid molecules may expressed in terms of a percentage calculated as follows: When a corresponding position in a complementary sequence relative to a reference sequence is occupied by a complementary base (e.g. a base that would be expected to base pair with the base in the reference sequence), then the sequences are complementary at that position. The percent of sequence complementarity can be maximized by aligning the compared sequences alongside each other, sliding them back and forth relative to each other, and conservatively introducing gaps in the sequences where necessary. The percent of sequence complementarity is calculated by counting the number of complementary aligning residues dividing by the total length of the aligned region, including gaps in both sequences, and multiplying by 100. Sequence complementarity would thus be expressed as, e.g., "60% complementary over 40 bases," or "57% identity over 30 amino acids." In the example indicated below, the compared sequence ("Comp": (SEQ ID NO: 1) sequence is 80% complementary over 44 bases compared to the reference ("Ref": (SEQ ID NO:2) sequence ( (35 complementary bases/44 bases)×100% ), where 44 is the total length of the aligned region, including gaps in both sequences.

tutions and/or deletions relative to the given RNA sequence over the analogous region). The analogous region is the region that is analogous between a DNA sequence and the given RNA sequence. Analogous sequences may be embedded within larger polynucleotides, thus a relatively long polynucleotide may have a portion that is analogous to a given RNA sequence, the portion being only a fraction of the total length of the polynucleotide. Similarly, the given RNA sequence may be only a fraction of the total length of the RNA molecule of which it is a part. The analogous region is typically at least about 10 bases long, more typically at least about 12 bases long, more typically at least about 15 bases long, still more typically at least about 20 bases long, or may be at least about 25 bases long. In various typical embodiments, the analogous region may be up to about 200 bases long, or up to about 120 bases long, up to about 100 bases long, up to about 80 bases long, up to about 60 bases long, up to about 45 bases long, or up to about 40 bases long.

An analogous sequence may have a percentage assigned to it as follows: when a corresponding position in an analogous DNA sequence relative to a given RNA sequence is occupied

```
Comp   UAUCCUCCAGUAACAUGUAAUGACGAAUGGAGGGUC-UUCUAAU   44 bases
       |||  |||||||||||  |||||||||||||| |||||  |  |||  35 compltry
Ref    AUA--AGGUCAUUGU--AUUACUGCUUACGACCCAGUAUAGUUA   44 bases
```

Note that the same sequences below (SEQ ID NO:1 and SEQ ID NO:2) may also be used to show that the DNA sequence is 90% complementary sequence over 31 bases.

by an analogous base (e.g. A for A, G for G, C for C and T for U), then the sequences are analogous at that position. The percent of analogous sequence can be maximized by aligning

```
Comp   UAUCCUCCAGUAACAUGUAAUGACGAAUGGAGGGUC-UUCUAAU   31 bases
       |||||||||||  ||||||||||||||| |||||             28 compltry.
Ref    AUA--AGGUCAUUGU--AUUACUGCUUACGACCCAGUAUAGUUA   31 bases
```

As used herein in the context of nucleotide sequences, 'analogous' references a DNA sequence that has the same sequence of bases as a given RNA sequence, except that T's in the DNA sequence substitute for U's in the RNA sequence. In particular embodiments in accordance with the present invention, a DNA sequence analogous to a first RNA sequence specifically hybridizes to a second RNA sequence under a given set of experimental conditions, such as using stringent hybridization conditions (or other conditions allowing for specific binding to occur), wherein the second RNA sequence is complementary to the first RNA sequence. Analogous sequences may include DNA sequences that are 'absolutely analogous' to a given RNA sequence (i.e. do not have any base insertions, deletions, or substitutions relative to the given RNA sequence) as well as sequences that are 'subthe analogous DNA sequence and the given RNA sequence alongside each other, sliding them back and forth, and conservatively introducing gaps in the sequences where necessary to account for insertions and deletions. The percent of analogous sequence is calculated by counting the number of analogous aligning residues, dividing by the total length of the aligned region, including gaps in both sequences, and multiplying by 100. Percent analogous sequence would thus be expressed as, e.g., "60% analogous sequence over 40 bases," or "57% analogous sequence over 30 amino acids." In the example indicated below, the DNA sequence (SEQ ID NO:3) is 75% analogous sequence over 44 bases compared to the RNA sequence (SEQ ID NO:4) ((33 bases/44 bases)× 100%), where 44 is the total length of the aligned region, including gaps in both sequences.

```
DNA   ATA--AGGTCATTGT--ATTACTGCTTACGACCCAGTATAGTTA   44 bases
      |||  |||||||||||  |||  |||||||||||  |||| |   |||  26 analog.
RNA   AUACCAGGUCAUUGUUGAUUGCUGCUUACGU-CCAG-AACAUUA   44 bases
``` stantially analogous' (i.e. having one or more relatively small (less than 10 bases, e.g. less than 5 bases, typically less than 3 bases, more typically a single base) base insertions, substi- Note that the same sequences below (SEQ ID NO:3 and SEQ ID NO:4) may also be used to show that the DNA sequence is 84% analogous sequence over 31 bases.

```
DNA  ATA--AGGTCATTGT--ATTACTGCTTACGACCCAGTATAGTTA  31 bases
        ||||||||||   |||  |||||||||||   ||||        26 analog.
RNA  AUACCAGGUCAUUGUUGAUUGCUGCUUACGU-CCAG-AACAUUA   31 bases
```

Accordingly, in certain embodiments of the present invention, a method of performing an array analysis of an RNA sample is provided. In certain embodiments, the invention provides a method of performing an array analysis wherein the method includes contacting the sample of RNA with an analogous DNA set to provide a DNA/RNA duplex. The analogous DNA set includes at least one sequence analogous to a small RNA. The DNA/RNA duplex is then contacted with an enzyme having a DNA:RNA nuclease activity to provide a digested RNA sample. The digested RNA sample is then contacted with an array for a time and under conditions sufficient to allow specific binding to the array, resulting in bound RNA and unbound RNA. The array includes capture agents that are specific for small RNAs. Typically, the array undergoes a subsequent washing to remove the unbound RNA, leaving the bound RNA on the array. The array may then be interrogated to obtain information about the sample of RNA.

The FIGURE illustrates an embodiment of a method in accordance with the present invention. As shown in the FIGURE, a sample of RNA 110 may include a variety of RNA molecules, including RNA molecules that lack any sequences complementary to small RNAs 112, RNA molecules that have one or more sequences complementary to small RNAs 114, and small RNAs 116. Sequences that are complementary to small RNAs are indicated at feature 118 (referenced as 'interfering sequences' herein), and sequences that are not complementary to small RNAs are indicated at feature 120. The sample of RNA 110 is then contacted 122 with an analogous DNA set 124. The analogous DNA set includes one or more oligodeoxynucleotides 126, each of the one or more oligodeoxynucleotides 126 comprising a sequence analogous to a corresponding small RNA. The oligodeoxynucleotides 126 hybridize to sequences that are complementary to small RNAs 118 (interfering sequences) to result in DNA/RNA duplexes 128. The DNA/RNA duplexes 128 are then contacted 130 with an enzyme having a DNA:RNA nuclease activity 132 to result in cleavage 134 of sequences that are complementary to small RNAs (interfering sequences), thereby providing a digested RNA sample 136.

Next, as indicated at arrow 140 the digested RNA sample 136 is contacted with an array 138. The array 138 includes an array support 142, to which capture agents 144 are bound, typically via a linker moiety 146. The capture agents 144 are bound on the array support 142 to form features 150, 152, and 154, typically separated by inter-feature areas 158. The capture agents 144 bound at each feature 150, 152, and 154 typically will exhibit specific binding with a particular target analyte, e.g. a particular small RNA 116. The array support 142 will include many features (three of which are shown at 150, 152, and 154) in a spatially distinct pattern, each feature bearing a capture agent 144 specific for a particular target analyte, e.g. a particular small RNA 116. As such, the array provides for analyzing binding of potentially many different target analytes in a spatially addressable fashion.

Contacting the digested RNA sample 136 with the array 138 results in small RNAs 116 from the digested RNA sample binding to the array 138 by binding to the capture agents 144. In the embodiment shown in the FIGURE, the capture agents of feature 154 are different from the capture agents at feature 152, and hence different small RNAs 116a, 116b are specifically bound at features 152 and 154, respectively. In the illustrated embodiment, the capture agents 144 present on the array support 142 are not specific for sequences of the digested RNA sample other than small RNA sequences, hence the small RNAs 116a, 116b are selectively bound to the array 138 ("bound RNA") while the remaining non-binding portion 156 ("unbound RNA") of the digested RNA sample remains free in solution (i.e. does not bind to the array) and can be washed off or otherwise removed from the array, e.g. under stringent washing conditions.

The array 142 is contacted with the digested RNA sample 136 under conditions sufficient to result in specific binding of at least a portion of the digested RNA sample (e.g. the small RNAs or other target analytes) while not significantly binding other components in the digested RNA sample which do not have corresponding capture agents on the array. In this context, binding of such other components is "significant" if such binding prevents meaningful data about binding of target analytes from being obtained from the array binding assay. Obtaining data from the array ("reading" the array) may be done using well known methods.

Embodiments in accordance with the present invention are now described in more detail, following the discussion set forth above. The sample of RNA 110 is contacted 122 with an analogous DNA set 124 under conditions selected to favor DNA/RNA duplex 128 formation over RNA/RNA duplex formation (e.g. resulting from small RNAs 116 in the sample of RNA 110 binding to the sequences that are complementary to small RNAs 118 (interfering sequences) ). Such conditions typically may be provided by adjusting the concentration of the analogous DNA set 124 to be in molar excess over the small RNAs 116 present in the sample when the sample of RNA 110 is contacted with the analogous DNA set 124. Appropriate concentrations of the oligodeoxynucleotides 126 in the analogous DNA set 124 may be readily determined given the disclosure herein and ordinary skill in the art, for example, by running a group of dilution experiments to determine what concentration of the components provides acceptable results. The temperature and buffer composition are selected to provide for stable DNA/RNA duplex 128 formation between the oligodeoxynucleotides 126 and the complementary sequences 118 in the sample of RNA 110. Certain embodiments favor formation of the DNA/RNA duplex over formation of RNA/RNA duplex to provide for greater differentiation in binding to the interfering sequences. In such embodiments, digestion of the interfering sequences with the enzyme having the DNA:RNA nuclease activity will be favored.

In some such embodiments the analogous DNA set may include an oligodeoxynucleotide that binds more tightly to an interfering sequence than the corresponding small RNA will. For example, the oligodeoxynucleotide may have fewer insertions, deletions, or substitutions relative to the interfering sequence than the corresponding small RNA has relative to the interfering sequence. As an example, a DNA/RNA duplex is made up of an oligodeoxynucleotide and an interfering sequence; and the interfering sequence may alternatively form an RNA/RNA duplex with the corresponding small RNA. If the small RNA has less sequence complementarity to the interfering sequence than the oligodeoxynucleotide does to the interfering sequence, it may be expected that formation of the DNA/RNA duplex may be favored over the RNA/RNA duplex, given an appropriate selection of hybridization conditions, e.g. stringent conditions. In this context "less sequence complementarity" references a lower percent sequence complementarity over a given number of bases, wherein the given number is typically an integer selected from the range from about 8 to about 45. As another example, in order to select an oligodeoxynucleotide that binds more tightly to an interfering sequence than the corresponding small RNA does, known sequence information (e.g. from a genomic database of the organism being investigated) about the small RNA and putative interfering sequence(s) is compared to design an oligodeoxynucleotide that selectively binds to the putative interfering sequence(s). Such selection and design of an oligodeoxynucleotide will be apparent from the description herein and need not be further discussed. In certain embodiments, selection of oligodeoxynucleotides may be based on experimental observation of binding to interfering sequences.

In typical embodiments, the DNA/RNA duplex is contacted with enzyme having the DNA:RNA nuclease activity to provide a digested RNA sample. This contacting is done under conditions sufficient to allow the enzyme to contact the DNA/RNA duplex and to cleave the RNA strand of the DNA/RNA duplex to provide the digested RNA sample. Under typical conditions in exemplary embodiments, the digested RNA sample will have RNA with fewer interfering sequences (e.g. sites complementary to and capable of binding to small RNA) compared to the sample of RNA. After the digested RNA sample is obtained, it may be analysed by any known method for analyzing samples containing RNA. Conditions for contacting the DNA/RNA duplex with the enzyme having the DNA:RNA nuclease activity are typically known in the literature or are routine and may also typically be obtained from the supplier of the enzyme having the DNA:RNA nuclease activity.

The enzyme having the DNA:RNA nuclease activity may be any enzyme known to be capable of specifically cleaving at DNA/RNA duplexes. The enzyme having a DNA:RNA nuclease activity should be selected such that the enzyme is capable of digesting at least a portion of the RNA molecule at the site of the DNA/RNA duplex (i.e. the portion of the sequence of the RNA molecule that is complementary to the DNA and is bound to the DNA via base-pairing interaction). "Digesting" in this regard references a cleavage of one or more internucleotide bonds in the RNA molecule at the site of the DNA/RNA duplex. "DNA:RNA nuclease activity" refers to an activity of an endoribonuclease that specifically hydrolyzes the phosphodiester bonds of RNA which is hybridized to DNA, but does not digest single or double-stranded RNA. Selection of the enzyme having a DNA:RNA nuclease activity will typically be based on availability of the enzyme and activity of the enzyme under the desired reaction conditions for the formation of the DNA/RNA duplex and the digestion of the RNA at the RNA/DNA duplex by the enzyme (e.g. temperature, pH, ionic strength, source of RNA, structural feature of RNA, concentration of RNA, presence of other materials (e.g. contaminants, salt, surfactant, other solvents) etc.) In typical embodiments, the enzyme having an DNA:RNA nuclease activity does not cause substantial digestion of RNA that is not part of a DNA/RNA duplex, i.e. the nuclease activity is specific for the DNA/RNA duplex. In this regard, "substantial digestion" refers to a loss of greater than 50% of observable signal relative to a control experiment under essentially similar conditions using an enzyme that does not cause digestion of RNA that is not part of a DNA/RNA duplex.

A typical example of such an enzyme having the DNA:RNA nuclease activity is RNase H, available from Pharmacia (Piscataway, N.J.). In certain embodiments, a thermostable enzyme having the DNA:RNA nuclease activity is employed, such an enzyme is HYBRIDASE thermostable RNase H, available from Epicentre (Madison, Wis.), or an RNase H obtained from *Thermus thermophilus*. See Guatelli et al., Proc. Nat. Acad. Sci. (1990) 87:1874-78; Bekkaoui et al., BioTechniques (1996) 20: 240-48. In particular embodiments, however, a non-thermostable enzyme is selected, allowing inactivation of the enzyme by a relatively simple heat treatment once the digestion of the DNA/RNA duplex is conducted. Thus, in some embodiments, a method in accordance with the present invention may include inactivating or removing the enzyme having the DNA:RNA nuclease activity after the enzyme has cleaved the DNA/RNA duplexes to provide the digested RNA sample, such as by heat inactivation or by using precipitation methods, chromatography methods, or other purification methods to effect a separation of the RNA in the RNA sample from the enzyme having the DNA:RNA nuclease activity.

RNase H is known to require as few as four paired bases in a DNA/RNA duplex to act as an endonuclease, thus the oligodeoxynucleotides of the analogous DNA set should each be at least four bases long. This may of course vary depending on the specific enzyme used. In typical embodiments, an oligodeoxynucleotide will be at least about 8 bases long, or at least about 10 bases long, or at least about 12 bases long, or at least about 14 bases long. In typical embodiments, an oligodeoxynucleotide may be up to about 20 bases long, or up to about 25 bases long, or up to about 30 bases long, or even longer, such as up to about 50 bases long, or up to about 100 bases long, or more. In certain embodiments, a single oligodeoxynucleotide may include a plurality of sequences analogous to small RNAs (e.g. concatenated together, optionally including 'spacer' sequences between the sequences analogous to small RNAs), wherein each of the plurality of sequences may be analogous to the same or different small RNAs.

In usual embodiments, the analogous DNA set comprises at least one sequence analogous to a small RNA. The small RNA is typically selected from the group consisting of a short interfering RNA (siRNA), microRNA (miRNA), tiny non-coding RNA (tncRNA) and a small modulatory RNA (smRNA). In certain embodiments, the small RNA is selected from an RNA that is less than about 100 bases long, e.g. less than about 60, 50, 40, 35 bases long. Typically the small RNA is at least about 10 bases long, more typically at least about 12 bases long, or at least about 15 bases long, or longer, although sizes or types of small RNAs other than those listed in this paragraph may be included in some embodiments in accordance with the present invention.

The analogous DNA set typically includes at least one, two, three, four, five, or more different oligodeoxynucleotides. In particular embodiments, each oligodeoxynucleotide comprises at least one sequence analogous to a small RNA. In some embodiments, the analogous DNA set includes at least 10, 15, 20, 25, 30, 40 or 50 different oligodeoxynucleotides, and may have up to about 100, 200, 300, 400, 1000 or more different oligodeoxynucleotides. In certain embodiments, the analogous DNA set includes oligodeoxynucleotides that are analogous to at least 5 different small RNAs. In an embodiment, the analogous DNA set is synthesized on a solid support followed by cleaving the synthesized DNA from the support. As an example, many different oligodeoxynucleotides may be synthesized in parallel, e.g. on a solid planar support or in multiwell plate holding insoluble supports such as beads, where the oligodeoxynucleotides are bound to the support(s) by a cleavable linker. See, e.g., Pon, RT, et al., Nucleic Acids Res. 32:923-631 (2004). When the synthesis is complete, the cleavable linker may be cleaved to release the set of oligodeoxynucleotides into solution. The solution containing the set of oligodeoxynucleotides is then recovered and used as a source of the analogous DNA set.

As mentioned herein, the analogous sequences may include one or more base insertions, deletions and/or substitutions relative to the small RNA. In particular embodiments, the analogous DNA set comprises at least one oligodeoxynucleotide comprising a sequence analogous to a small RNA, wherein the sequence includes one or more base insertions, deletions and/or substitutions relative to the small RNA.

In particular embodiments, the oligodeoxynucleotides of the analogous DNA set are selected such that the DNA/RNA duplexes formed will have similar thermal stabilities. The melting temperature ('$T_m$') of the DNA/RNA duplexes should be high enough to eliminate or reduce any non-specific binding (e.g. preventing non-complementary sequences from forming double-stranded structures). In such embodiments, the melting temperatures of at least 80% of the DNA/RNA duplexes will be within about 15° C. of each other, typically within about 12° C. of each other, about 10° C. of each other, or about 5° C. of each other. In such embodiments, the DNA/RNA duplexes have a melting temperature for their respective targets in a range of about 15° C., within about 10° C., or within about 5° C. of each other. In certain embodiments, the difference between the maximum and minimum melting temperatures is less than about 20° C., less than about 15° C., less than about 10° C., or less than about 5° C. In some embodiments, oligodeoxynucleotide sequences may be selected based on experimental determinations of their melting temperatures or calculations of their theoretical melting temperatures; or putative oligodeoxynucleotide sequences may first be selected based on calculations of their theoretical melting temperatures and then be confirmed experimentally. Methods for determining the melting temperature of nucleic acid duplexes are known in the art. See for example, Sambrook and Russell (2001) Molecular Cloning: A Laboratory Handbook, 10.38-10.41 and 10.47, which is incorporated by reference in its entirety.

A value for melting temperature can be determined mathematically using equations and algorithms known in the art. For duplex oligonucleotides shorter than 25 bp, "The Wallace Rule" can be used in which:

$T_m$ (in ° C.)=2(A+T)+4(C+G), where (A+T)—the sum of the A and T residues in the oligonucleotide, (C+G)—the sum of G and C residues in the oligonucleotide (see Wallace et al., Nucleic Acids Res. (1979) 6: 3543-3557). Computer programs for estimating $T_m$ are also available (see, e.g., Le Novere, Bioinformatics (2001) 17(12): 1226-1227). VisualOmp (DNA Software, Inc., Ann Arbor, Mich.) is an example of commercially available software for calculating nucleic acid duplex melting temperature.

A method in accordance with the present invention may further include contacting the digested RNA sample with an enzyme having a DNA nuclease activity to result in digestion of the analogous DNA set. "DNA nuclease activity" refers to an activity of an endonuclease that nonspecifically cleaves DNA, including cleaving single stranded DNA and double stranded DNA, but does not digest single or double-stranded RNA. Selection of the enzyme having a DNA nuclease activity will typically be based on availability of the enzyme and activity of the enzyme under the desired reaction conditions for the digestion of the DNA by the enzyme (e.g. temperature, pH, ionic strength, presence or concentration of RNA, presence of other materials (e.g. contaminants, salt, surfactant, other solvents) etc.) In typical embodiments, the enzyme having a DNA nuclease activity does not cause substantial digestion of RNA, i.e. the nuclease activity is specific for the DNA. One example of an enzyme having a DNA nuclease activity is DNase I, available from Pharmacia, although other enzymes having DNA nuclease activity may be selected instead. In some embodiments, the analogous DNA set may compete, e.g. on an array, with the small RNAs in the digested RNA sample for binding sites that are complementary for small RNAs. Digestion of the analogous DNA set reduces the competition, enabling a more sensitive assay for the small RNAs in the digested RNA sample. Conditions employed for contacting the digested RNA sample with an enzyme having a DNA nuclease activity are typically known in the art, and need not be further detailed here. Other experimental parameters may be selected based on known ranges for the experimental parameters or determined through routine experimentation based on, e.g. efficacy of the digestion reaction. Such other experimental parameters may include, e.g. temperature, pH, ionic strength, source of RNA and/or enzyme, structural feature of RNA, concentration of RNA, concentration of DNA, presence of other materials (e.g. contaminants, salt, surfactant, other solvents) etc.

The sample of RNA may be obtained from any source. For example, the sample of RNA may be any RNA sample, typically a sample containing RNA that has been isolated from a biological source, e.g. any plant, animal, yeast, bacterial, or viral source, or a non-biological source, e.g. chemically synthesized. In particular embodiments, the sample of RNA includes one or more short RNAs, such as e.g. short interfering RNAs (siRNAs), microRNAs (miRNA), tiny non-coding RNAs (tncRNA) and small modulatory RNA (smRNA). See Novina et al., Nature (2004) 430: 161-164. In particular embodiments, the sample includes isolated small RNAs, e.g. the sample results from an isolation protocol for small RNA such as one or more of those listed in this paragraph. In certain embodiments, the small RNA targets may include isolated miRNAs, such as those described in the literature and in the public database accessible via the website located at >>http://www.sanger.ac.uk/cgi-bin/Rfam/mirna/browse.pl<<. In particular embodiments, the sample includes isolated small RNAs, e.g. the sample results from an isolation protocol for small RNA, especially RNAs less than about 500 bases long, e.g. less than about 400 bases long, less than about 300 bases long, less than about 200 bases long, less than about 100 bases long, or less than about 50 bases long. In some embodiments, the sample of RNA may be a whole RNA fraction isolated from a biological source and includes messenger RNA and small RNA. Such samples including a diverse set of RNAs, such as a whole RNA fraction, may be referenced herein as "complex" RNA samples.

In certain embodiments, the invention may further include providing an observable label that may be observed to obtain information relating to the sample of RNA, such as the presence of particular sequences of RNA present in the sample. The observable label may be any observable label known in the art, e.g. a chromophore, a fluorescent label, a spin label, a radioisotope label, a mass label, a sequence label, a chemically reactive tag, an affinity label, or any other known label. In particular embodiments, the observable label is a fluorophore selected from the group consisting of Cy3, Cy5, and an Alexa dye. Further examples of observable labels include any commercially available fluorophores that can be conjugated to mononucleotides or polynucleotides, e.g. dyes from Molecular Probes (Eugene , OR and Leiden, The Netherlands) such as the Alexa Fluor series (example: Alexa 350, Alexa 430, Alexa 532, Alexa 546, Alexa 568, and Alexa 594) and the series of BODIPY conjugates. Other examples include: Tamra, Fluorescein, carboxyfluorescene, rhodamine, carboxyrhodamine, CY series, Oyster series, 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), and 6-carboxy-X-rhodamine (ROX or R). More information about commercially available dyes for oligonucleotide conjugation can be found at the website located at >>http://www.synthegen.com<<. Any such dyes may potentially be used in accordance with the methods described herein. Such labels typically are well known in the art.

In particular embodiments, the RNA in the sample may already be labeled when the sample is obtained, e.g. the sample may be isolated from an organism grown in a radiolabeled medium. In an embodiment, the sample of RNA comprises RNA that has an observable label attached thereto, and this labeled sample of RNA is then contacted with an analogous DNA set to provide a DNA/RNA duplex. In particular embodiments, the RNA may be labeled by following a known labeling protocol. In some such embodiments, before the sample of RNA is contacted with the analogous DNA set, the sample of RNA is subjected to a labeling treatment that results in the RNA in the sample of RNA being labeled with an observable label. A particularly contemplated labeling protocol is described in copending application Ser. No. 11/048,255 entitled "RNA Labeling Method" and filed by Wang on Jan. 31, 2005. In an embodiment, the digested RNA sample is labeled with an observable label after the RNA sample has been contacted with the enzyme having the DNA:RNA nuclease activity. Depending on the application, the presence of the observable label in the analogous DNA set may interfere with the analysis of the sample of RNA; therefore, in certain embodiments the analogous DNA set lacks the observable label.

In certain other embodiments, the analogous DNA set may be labeled with an observable label (possibly, though not necessarily, the same observable label used to label the RNA). In certain embodiments, the analogous DNA set may be labeled (i.e. the members of the analogous DNA set, e.g. the oligonucleotides, may be labeled) with a first observable label, such as Cy3, and the RNA sample may be labeled with a second observable label, such as Cy5, to give distinguishable signals upon observation of the labels. Such choice of first and second labels is referred to herein as "distinguishable" labels in that the labels that can be independently detected and measured, even when the labels are mixed. In other words, the amounts of label present (e.g., the amount of fluorescence) for each of the labels are separately determinable, even when the labels are co-located (e.g., in the same tube, in the same duplex molecule, or in the same feature of an array). Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), fluorescein and Texas red (Dupont, Boston, Mass.) and POPRO3 and TOPRO3 (Molecular Probes, Eugene, Oreg.). Further suitable distinguishable detectable labels may be described in Kricka et al. (Ann Clin Biochem. 39:114-29, 2002).

In some embodiments, only one observable label moiety is attached to a labeled polynucleotide (e.g. labeled RNA molecule or labeled DNA molecule). In such embodiments, the labeled polynucleotide will consist essentially of the polynucleotide labeled with a single label moiety (i.e. each labeled polynucleotide molecule will have only one observable label moiety attached—referenced herein as a "singly-labeled" polynucleotide). This potentially provides increased ease of use in quantitative methods using the labeled polynucleotide.

In other embodiments, a labeled polynucleotide (e.g. labeled RNA molecule or labeled DNA molecule) may have a plurality of observable label moieties. Thus, the labeled polynucleotide will consist essentially of the polynucleotide labeled with a plurality of label moieties. This increased labeling of the polynucleotide may provide for greater sensitivity in analyses using the labeled polynucleotide.

In particular embodiments in accordance with the present invention, after the digested RNA sample is obtained, the digested RNA sample may be contacted with an array and a binding pattern observed on the array. Accordingly, methods of performing an array analysis of an RNA sample are provided. In certain embodiments, the invention provides a method of performing an array analysis wherein the method includes contacting the sample of RNA with at least one DNA sequence analogous to a small RNA under conditions sufficient to allow formation of a DNA/RNA duplex. The DNA/RNA duplex is then contacted with an enzyme having a DNA:RNA nuclease activity to provide a digested RNA sample. The digested RNA sample is then contacted with an array under conditions sufficient to provide for specific binding to the array. The array typically is then interrogated to provide data on binding of the digested RNA sample to the array.

In typical embodiments, the array includes capture agents bound to an array support, wherein the capture agents are specific for small RNAs suspected of being in the sample of RNA, e.g. wherein the capture agents are complementary to small RNAs suspected of being in the sample of RNA. Note that, in certain embodiments, an array that has a plurality of capture agents bound to an array support (each of the plurality of capture agents specific for a small RNA) may also include other capture agents bound to the array support wherein each of the other capture agents is not specific for a small RNA (i.e. is specific for some other target). Contacting the digested RNA sample with the array is conducted under conditions sufficient to result in specific binding of at least a portion of the digested RNA sample to the array. The specific binding results in a binding pattern that may be observed by interrogating the array to give information about the presence and/or concentration of small RNAs in the sample of RNA. In certain embodiments, the array includes capture agents bound to an array support, wherein the capture agents are complementary to sequences that are proximal to interfering sequences. "Sequences that are proximal to interfering sequences" are those sequences on the same strand of RNA on which the interfering sequence is located, wherein said sequences are located within about 500 bases from the interfering sequence, typically within about 300 bases, more typically within about 200 bases, still more typically within about 100 bases, yet more typically within about 50 bases.

Standard hybridization techniques (using stringent hybridization conditions) are used to hybridize a digested RNA sample to a nucleic acid array. Several guides to general techniques are available, e.g., Tijssen, Hybridization with Nucleic Acid Probes, Parts I and II (Elsevier, Amsterdam 1993). For descriptions of techniques suitable for in situ hybridizations, see Gall et al. Meth. Enzymol., 21:470-480 (1981); and Angerer et al. in Genetic Engineering: Principles and Methods (Setlow and Hollaender, Eds.) Vol 7, pgs 43-65 (Plenum Press, New York 1985). See also U.S. Pat. Nos. 6,335,167; 6,197,501; 5,830,645; and 5,665,549; the disclosures of which are herein incorporated by reference. Hybridizing the sample to the array is typically performed under stringent hybridization conditions, as described herein and as known in the art. Selection of appropriate conditions, including temperature, salt concentration, polynucleotide concentration, time (duration) of hybridization, stringency of washing conditions, and the like will depend on experimental design, including source of sample, identity of capture agents, degree of complementarity expected, etc., and are within routine experimentation for those of ordinary skill in the art to which the invention applies.

Following hybridization, the array-surface bound polynucleotides are typically washed to remove unbound and not tightly bound labeled nucleic acids. Washing may be performed using any convenient washing protocol, where the washing conditions are typically stringent, as described above.

Following hybridization and washing, as described above, the hybridization of the labeled target nucleic acids to the capture agents is then detected using standard techniques of reading the array, i.e. the array is interrogated. Reading the resultant hybridized array may be accomplished by illuminating the array and reading the location and intensity of resulting fluorescence at each feature of the array to detect any binding complexes on the surface of the array. For example, a scanner may be used for this purpose, which is similar to the AGILENT MICROARRAY SCANNER available from Agilent Technologies, Palo Alto, Calif. Other suitable devices and methods are described in U.S. patent application Ser. No. 09/846125 "Reading Multi-Featured Arrays" by Dorsel et al.; and U.S. Pat. No. 6,406,849. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). In the case of indirect labeling, subsequent treatment of the array with the appropriate reagents may be employed to enable reading of the array. Some methods of detection, such as surface plasmon resonance, do not require any labeling of nucleic acids, and are suitable for some embodiments.

Results from the reading or evaluating may be raw results (such as fluorescence intensity readings for each feature in one or more color channels) or may be processed results (such as those obtained by subtracting a background measurement, or by rejecting a reading for a feature which is below a predetermined threshold, normalizing the results, and/or forming conclusions based on the pattern read from the array (such as whether or not a particular target sequence may have been present in the sample, or whether or not a pattern indicates a particular condition of an organism from which the sample came)).

In certain embodiments, results from interrogating the array are used to assess the level of binding of the population of labeled nucleic acids to capture agents on the array. The term "level of binding" means any assessment of binding (e.g. a quantitative or qualitative, relative or absolute assessment) usually done, as is known in the art, by detecting signal (i.e., pixel brightness) from a label associated with the sample nucleic acids, e.g. the digested sample is labeled. The level of binding of labeled nucleic acid to capture agent is typically obtained by measuring the surface density of the bound label (or of a signal resulting from the label).

In an embodiment, results from interrogating the array are compared to a control result, e.g. a result obtained from conducting an assay under similar conditions but changing or omitting one or more elements of the assay. For example, the control result may be obtained by omitting the RNA sample, changing the source of the RNA sample (e.g. human vs. mouse, further e.g. diseased vs. non-diseased source), changing the hybridization conditions, changing a capture agent, or any other way of obtaining a control result known in the art. Methods of obtaining such control results are well known and need not be described in further detail herein. In certain embodiments, the control result may be obtained from interrogating a control feature on the same array used to contact the digested RNA sample.

In certain embodiments, a surface-bound polynucleotide may be assessed by evaluating its binding to two populations of nucleic acids that are distinguishably labeled. In these embodiments, for a single surface-bound polynucleotide of interest, the results obtained from hybridization with a first population of labeled nucleic acids may be compared to results obtained from hybridization with the second population of nucleic acids, usually after normalization of the data. The results may be expressed using any convenient means, e.g., as a number or numerical ratio, etc.

In typical embodiments of methods in accordance with the present invention, the digested RNA sample may be labeled, e.g. with Cy5 or Cy3, and hybridized onto microarrays as follows: The labeled RNA is desalted (e.g. with BioRad Micro Bio-Spin™ 6, as directed by BioRad instructions) to remove excess observable label remaining from the labeling reaction. The desalted sample of RNA is added to solution containing water and carrier (25-mer DNA with random sequence). The resulting solution is heated at about 100° C. for approximately 1 minute per 10 microliters of solution, and then immediately cooled on ice. The cooled solution is then added to hybridization buffer and mixed carefully. The final solution is then contacted with the array, e.g. in a SureHyb hybridization chamber (Agilent Part Number:G2534A), and placed on rotisserie of hybridization oven overnight. The hybridization temperature is typically in the range from about 50° C. to about 60° C., although temperatures outside this range (e.g. in the range from about 30° C. to about 65° C.) may be used depending on the other experimental parameters, e.g. hybridization buffer composition and wash conditions. After the hybridization is complete, the array is washed thoroughly and dried with nitrogen as needed. The array is scanned (e.g. with an Agilent Scanner, Agilent Product Number: G2565BA). The data is then evaluated (e.g. using Agilent Feature Extraction Software, Agilent Product Number: G2567AA) for hybridization efficiency and specificity. Data may be further analyzed, e.g. using Spotfire software and Microsoft Excel.

Certain embodiments in accordance with the present invention provide a method for detecting a small RNA in a sample of RNA, wherein the sample contains an interfering sequence complementary to said small RNA. In such embodiments, the method includes contacting the sample of RNA with an oligodeoxynucleotide to provide a DNA/RNA duplex, wherein the oligodeoxynucleotide is complementary to the interfering sequence. The DNA/RNA duplex is then contacted with an enzyme having a DNA:RNA nuclease activity to provide a digested RNA sample. The digested RNA sample is then contacted with a capture agent under conditions sufficient to provide for specific binding to the capture agent to result in the small RNA bound to the capture agent. The small RNA bound to the capture agent is then detected.

Also provided by the subject invention are kits for practicing the subject methods, as described above. The subject kits include at least an analogous DNA set. In certain embodiments the subject kits may also include reagents for isolating RNA from a source to provide the sample of RNA. In some embodiments the subject kits optionally also include one or more constituents selected from reagents for labeling RNA, reagents for contacting the sample of RNA with the analogous DNA set, enzymes for use with the subject methods such as described above, control samples, an array having a plurality of capture agents (each of the plurality of capture agents specific for a small RNA), reagents for performing an array hybridization, combinations thereof, etc. The various components of the kit may be present in separate containers or certain compatible components may be precombined into a single container, as desired.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a suitable material, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable material.

The practice of the present invention will employ, unless otherwise indicated, conventional techniques of synthetic organic chemistry, biochemistry, molecular biology, and the like, which are within the skill of the art. Such techniques are explained fully in the literature. Unless otherwise defined herein, all technical and scientific terms used herein have the same meaning as commonly understood by one of ordinary skill in the art to which the invention belongs. The description herein is put forth so as to provide those of ordinary skill in the art with a complete disclosure of the methods and compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

In particular embodiments the present invention thus provides methods of treating a sample of RNA to remove sequences of RNA that are complementary to small RNAs (i.e. "interfering sequences") and then performing array hybridization analysis. It is expected that the present invention may provide a sensitive assay system for the detection of small RNA in samples of RNA. Such samples of RNA may be obtained from sources reflecting different developmental stages, tissue samples, disease states, as well as any individual and/or abnormal variations.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties, provided that, if there is a conflict in definitions, the definitions provided herein shall control.

What is claimed is:

1. A method of analyzing RNAs comprising:
   a) contacting a sample comprising RNAs and interfering sequences that are complementary to said RNAs with an analogous DNA set to provide a DNA/RNA duplex comprising an analogous DNA of said set and a complementary interfering sequence, wherein the analogous DNA set comprises at least one sequence comprising the same sequence of bases as an RNA of said sample, except that uracils in the sequence of said RNA are substituted with thymines, and wherein said sample is isolated from a biological source;
   b) contacting the DNA/RNA duplex with an enzyme having a DNA:RNA nuclease activity to provide a digested RNA sample;
   c) contacting the digested RNA sample with an array of probes that are complementary to the analogous DNAs of said analogous DNA set under conditions sufficient to provide for specific binding of said RNA to a probe of said array; and
   d) interrogating the array.

2. The method of claim 1, wherein contacting the digested RNA sample with an array results in bound RNA and unbound RNA, wherein the method further comprises, prior to interrogating the array, washing the array to remove the unbound RNA.

3. The method of claim 2, wherein interrogating the array includes detecting a signal indicating the presence of the bound RNA to give raw results and processing the raw results by one or more manipulations selected from the group consisting of subtracting a background measurement, rejecting a measurement which is below a predetermined threshold, normalizing the raw results, and forming conclusions based on the raw results.

4. The method of claim 2, wherein the bound RNA comprises an observable label, and wherein interrogating the array comprises detecting a signal from the observable label and using the signal to assess binding of the bound RNA to the array.

5. The method of claim 4, wherein the observable label is selected from a chromogenic moiety, a fluorophore, a mass label, a spin label, or a radiolabel.

6. The method of claim 4, wherein the analogous DNA set lacks the observable label.

7. The method of claim 1, further comprising, prior to contacting the digested RNA sample with array, labeling the digested RNA sample with an observable label.

8. The method of claim 1, wherein the digested RNA sample comprises two populations of nucleic acids that are distinguishably labeled, and wherein interrogating the array comprises detecting distinguishable signals from the distinguishably labeled populations of nucleic acids and using the distinguishable signals to assess binding of the distinguishably labeled populations of nucleic acids.

9. The method of claim 1, wherein the array comprises a plurality of capture agents bound to an array support, wherein each of the plurality of capture agents is specific for a small RNA.

10. The method of claim 1, wherein the array comprises a plurality of capture agents bound to an array support, wherein each of the plurality of capture agents is complementary to a sequence that is proximal to an interfering sequence.

11. The method of claim 1, wherein the conditions sufficient to provide for specific binding to the array include stringent hybridization conditions.

12. The method of claim 1, wherein the analogous DNA set comprises a plurality of oligodeoxynucleotides, each of the plurality of oligodeoxynucleotides comprising a sequence analogous to a small RNA.

13. The method of claim 12, wherein each of the plurality of oligodeoxynucleotides is at least about 8 bases long and is up to about 100 bases long.

14. The method of claim 1, wherein the analogous DNA set comprises at least 5 different oligodeoxynucleotides, each of the oligodeoxynucleotides comprising a sequence analogous to a small RNA.

15. The method of claim 1, wherein the at least one sequence includes one or more base insertions, deletions and/or substitutions relative to the RNA.

16. The method of claim 1, wherein said RNA is selected from the group consisting of a short interfering RNA (siRNA), microRNA (miRNA), tiny non-coding RNA (tncRNA) and a small modulatory RNA (smRNA).

17. The method of claim 1, wherein the sample of RNA comprises isolated RNA having length less than about 500 bases.

18. The method of claim 1, further comprising:
prior to contacting the digested RNA sample with the array, contacting the digested RNA sample with an enzyme having a DNA nuclease activity to result in digestion of the analogous DNA set.

19. A method for analyzing a RNA comprising:
contacting a sample of RNA comprising an interfering sequence complementary to said RNA with an oligodeoxynucleotide to provide a DNA/RNA duplex, wherein the oligodeoxynucleotide is complementary to the interfering sequence and analogous to the RNA, and wherein said oligodeoxynucleotide has the same sequence of bases as said RNA, except that uracils in the sequence of said small RNA are substituted with thymines, and wherein said sample is isolated from a biological source;
contacting the DNA/RNA duplex with an enzyme having a DNA:RNA nuclease activity to provide a digested RNA sample;
contacting the digested RNA sample with a capture agent under conditions sufficient to provide for specific binding to the capture agent to result in the RNA bound to the capture agent; and
detecting the RNA bound to the capture agent.

20. The method of claim 1, wherein said at least one sequence analogous to a small RNA is a DNA sequence which is the same as an RNA sequence of the small RNA, without any base insertions, deletions, or substitutions relative to the RNA sequence, except that T's in the DNA sequence substitute for U's in the RNA sequence.

21. The method of claim 1, wherein said at least one sequence analogous to said RNA is substantially analogous, over an analogous region, to said RNA.

22. The method of claim 1, wherein said sample comprises a small RNA.

23. The method of claim 19, wherein said sample comprises a small RNA.

24. The method of claim 19, wherein said oligodeoxynucleotide has a DNA sequence which is the same as an RNA sequence of the RNA, without any base insertions, deletions, or substitutions relative to the RNA sequence, except that T's in the DNA sequence substitute for U's in the RNA sequence.

* * * * *

UNITED STATES PATENT AND TRADEMARK OFFICE
CERTIFICATE OF CORRECTION

PATENT NO.       : 7,718,365 B2
APPLICATION NO.  : 11/178064
DATED            : May 18, 2010
INVENTOR(S)      : Hui Wang It is certified that error appears in the above-identified patent and that said Letters Patent is hereby corrected as shown below:

On the face page, in field (56), under "Other Publications", in column 2, line 26, delete "Olgoribonucleotide" and insert -- Oligoribonucleotide --, therefor.

Signed and Sealed this

Twentieth Day of July, 2010

David J. Kappos
*Director of the United States Patent and Trademark Office*

SEQUENCE LISTING

```
<160> NUMBER OF SEQ ID NOS: 4

<210> SEQ ID NO 1
<211> LENGTH: 43
<212> TYPE: RNA
<213> ORGANISM: Artificial
<220> FEATURE:
<223> OTHER INFORMATION: artificial exemplary sequence for
      complementary/analogous sequence definitions

<400> SEQUENCE: 1
uauccuccag uaacauguaa ugacgaaugg agggucuucu aau                    43

<210> SEQ ID NO 2
<211> LENGTH: 40
<212> TYPE: RNA
<213> ORGANISM: Artificial
<220> FEATURE:
<223> OTHER INFORMATION: artificial exemplary sequence for
      complementary/analogous sequence definitions

<400> SEQUENCE: 2
```

-continued

```
auaaggucau uguauuacug cuuacgaccc aguauaguua                        40

<210> SEQ ID NO 3
<211> LENGTH: 40
<212> TYPE: DNA
<213> ORGANISM: Artificial
<220> FEATURE:
<223> OTHER INFORMATION: artificial exemplary sequence for
      complementary/analogous sequence definitions

<400> SEQUENCE: 3
ataaggtcat tgtattactg cttacgaccc agtatagtta                        40

<210> SEQ ID NO 4
<211> LENGTH: 42
<212> TYPE: RNA
<213> ORGANISM: Artificial
<220> FEATURE:
<223> OTHER INFORMATION: artificial exemplary sequence for
      complementary/analogous sequence definitions

<400> SEQUENCE: 4
auaccagguc auuguugauu gcugcuuacg uccagaacau ua                     42
```